United States Patent [19]

Baron et al.

[11] Patent Number: 4,605,774

[45] Date of Patent: Aug. 12, 1986

[54] PREPARATION OF BIS(4-HYDROXYPHENYL THIO)BENZENES

[75] Inventors: Arthur L. Baron; Parameswar Sivaramakrishnan, both of New Martinsville, W. Va.

[73] Assignee: Mobay Corporation, Pittsburgh, Pa.

[21] Appl. No.: 943,517

[22] Filed: Sep. 18, 1978

[51] Int. Cl.$^4$ .................................. C07C 148/00
[52] U.S. Cl. ........................... 568/48; 528/44; 528/86; 528/176; 528/196; 528/212
[58] Field of Search ............ 260/609 F; 528/196; 568/48

[56] References Cited

U.S. PATENT DOCUMENTS

| | | | |
|---|---|---|---|
| 2,288,282 | 6/1942 | Huismann | 260/607 AR |
| 3,069,384 | 12/1962 | Coffield | 568/48 |
| 3,269,986 | 8/1966 | Goldberg | 260/49 |
| 3,271,367 | 9/1966 | Schnell et al. | 528/196 |
| 3,419,526 | 12/1968 | Schnell et al. | 528/196 |
| 3,770,832 | 11/1973 | Leslie et al. | 260/607 AR |
| 3,809,682 | 5/1974 | Studinka et al. | 260/61 |
| 3,824,293 | 7/1974 | Brode | 568/33 |
| 3,843,600 | 10/1974 | Robin et al. | 260/609 F |
| 3,931,335 | 1/1976 | Cisney et al. | 568/48 |
| 4,075,119 | 2/1978 | Schmidt et al. | 252/182 |

FOREIGN PATENT DOCUMENTS

| | | | |
|---|---|---|---|
| 2055452 | 5/1972 | Fed. Rep. of Germany | 528/196 |
| 2721595 | 12/1977 | Fed. Rep. of Germany | 528/196 |
| 1153035 | 5/1969 | United Kingdom . | |
| 1153528 | 5/1969 | United Kingdom . | |
| 1151042 | 5/1969 | United Kingdom . | |
| 1190135 | 4/1970 | United Kingdom . | |
| 1234301 | 6/1971 | United Kingdom . | |
| 1264900 | 2/1972 | United Kingdom . | |

OTHER PUBLICATIONS

R. Hawkins, Chem. Abstracts 84: 165535 a (1976).
G. Leandri et al., Chem. Abstracts 51: 8685i–8686f (1957).
Fine Chemicals Patents Journal 6, No. 43, German 5: 2 (10/28/66).
R. Nounan, Principles of Organic Synthesis, Methuen & Co., London, p. 356.
R. Fuson, Reactions of Organic Compounds, John Wiley & Sons, N.Y., pp. 40–41.

*Primary Examiner*—Donald G. Daus
*Assistant Examiner*—Mary E. Ceperley
*Attorney, Agent, or Firm*—Gene Harsh; Joseph C. Gil; Thomas W. Roy

[57] ABSTRACT

The present invention relates to the novel monomers generically identified as bis(4-hydroxyphenyl thio)benzenes, to a process for their production and to their use in the preparation of polycarbonates, polyurethanes, polyesters, polysulfones and polyethers.

2 Claims, No Drawings

PREPARATION OF BIS(4-HYDROXYPHENYL THIO)BENZENES

SUMMARY OF THE INVENTION

The present invention comprises novel monomers generically identified as bis(4-hydroxyphenyl thio)benzenes of the structural formula:

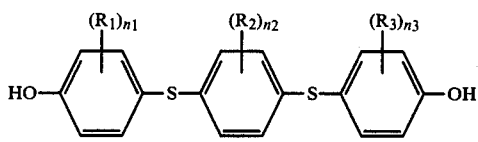

wherein $R_1$, $R_2$ and $R_3$, which may be the same or different, are $C_1$–$C_4$-alkyl, Cl or Br, and $n_1$, $n_2$ and $n_3$, which may be the same or different, are 0, 1 or 2, to a process for their synthesis and to polycarbonates, polyurethanes, polyesters, polysulfones and polyethers prepared from these novel monomers.

DETAILED DESCRIPTION OF THE INVENTION

The bis(4-hydroxyphenyl thio)benzenes of the present invention have the general structural formula:

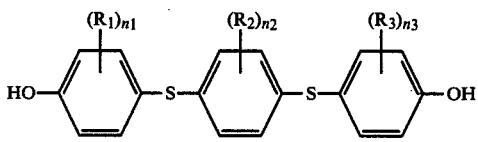

wherein $R_1$, $R_2$ and $R_3$, which may be the same or different, are $C_1$–$C_4$-alkyl, Cl or Br, and $n_1$, $n_2$ and $n_3$, which may be the same or different, are 0, 1 or 2.

A route suitable for the synthesis of the generic bis(4-hydroxyphenyl thio)benzenes is illustrated by the following general reaction scheme for the synthesis of bis(4-hydroxyphenyl thio)benzenes ($n_1$–$n_3$=0), the preferred monomer of the present invention:

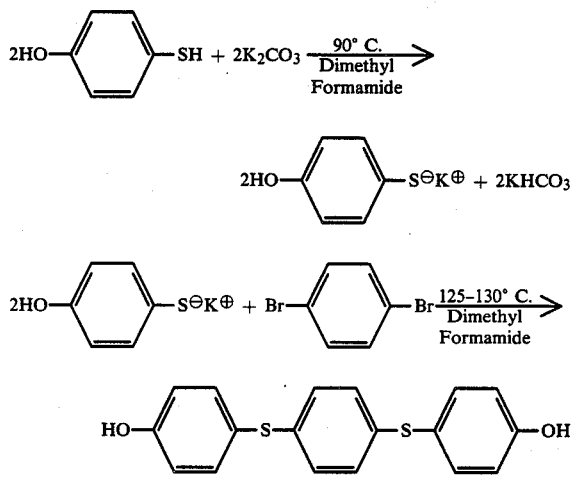

As indicated in the above reaction scheme, 4-mercaptophenol is reacted with p-dibromobenzene in the presence of potassium carbonate and dimethylformamide to produce the preferred bis(4-hydroxphenyl thio)benzene of the present invention. The resulting monomer is recovered as a precipitate and is then separated and dried.

When the reaction is performed on 0.1 mol of p-dibromo benzene, only the desired monomer is formed in 87.8% yield. Scale up of the reaction on a 3.0 mol basis produced a mixture of the desired monomer and the expected by-product, 4'-bromo, 4-hydroxy diphenyl sulfide, in the ratio of 55/45 weight %.

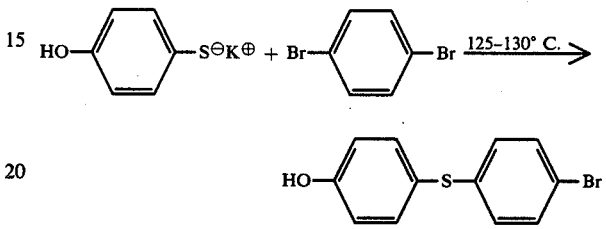

Separation of bis(4-hydroxyphenyl thio)benzene from 4'-bromo-4-hydroxy diphenyl sulfide is effected by difference in solubility. 4'-bromo-4-hydroxy diphenyl sulfide being soluble in cyclohexane is removed by Soxhlet extraction of the reaction mixture. Soxhlet extraction is a well-known continuous type of extraction practiced in organic chemistry to separate a mixture having one component possessing solubility in solvent.

The generic bis(4-hydroxyphenyl thio)benzenes of the invention are useful as monomers or one of the comonomers in the synthesis of polycarbonates, polyurethanes, polyesters, polysulfones, polyethers and other polymers.

Such polycarbonates may be produced using the novel monomers of the invention by well-known methods, such as disclosed in U.S. Pat. Nos. 2,964,794; 2,970,131; 2,991,237; 2,999,835; 2,999,846; 3,028,365; 3,153,008; 3,187,065; 3,215,668 and 3,248,414, all incorporated herein by reference and in the monograph H. Schnell, *Chemistry and Physics of Polycarbonates,* Interscience Publishers, New York, N.Y., 1964.

Such polyurethanes may be produced using the novel monomers of the invention by well-known methods, such as disclosed in U.S. Pat. Nos. 2,266,777; 2,284,637; 2,284,296; 2,511,544, all incorporated herein by reference and in the text *Polyurethanes: Chemistry and Technology,* Vol. 1, S. H. Saunders and K. C. Frisch, Interscience Publishers, New York, N.Y., 1964.

Such polyesters may be produced using the novel monomers of the invention by well-known methods, such as disclosed in U.S. Pat. Nos. 2,980,650; 3,185,668; 3,185,670 and 3,268,482, all incorporated herein by reference, and in the text *Polyesters* (two parts), edited by Norman G. Gaylord, Interscience Publishers, New York, 1962.

Such polysulfones may be produced using the novel monomers of the invention by well-known methods, such as disclosed in U.S. Pat. Nos. 3,236,808; 3,236,809; 3,409,599 and 3,742,087, all incorporated herein by reference.

Such polyethers may be produced using the novel monomers of the invention by well-known methods, such as disclosed in U.S. Pat. Nos. 1,922,459; 2,253,723; 2,991,313 and 3,651,151, all incorporated herein by reference, and in the text *Polyethers*, (three parts), edited by Norman G. Gaylord, Interscience Publishers, New York, 1962.

The invention will be further illustrated, but is not intended to be limited by the following examples.

EXAMPLES

EXAMPLE 1

Synthesis of Bis(4-Hydroxyphenyl Thio)Benzene

4-Mercaptophenol (756 g; 6.0 moles) was added to a slurry of anhydrous potassium carbonate (910 g; 6.59 mols, 10% excess) and 7 liters of distilled dimethyl formamide contained in a 12 liter stirred resin reactor. The reaction was carried out under dry nitrogen atmosphere. The mixture was slowly heated to 60° C. at which time a yellow coloration to the reaction mixture was observed. This is due to the formation of potassium salt of 4-mercaptophenol. The reaction mixture was held at 90° C. for 3 hours. Para dibromobenzene (708 g; 3 moles) dissolved in 1.5 liters of distilled dimethyl formamide was added to the reaction mixture through an addition funnel in ½ hour. The reaction temperature was raised to 130° C. and maintained at this temperature for 20 hours. The reaction mixture was filtered through a Buchner funnel to remove potassium bicarbonate and unreacted potassium carbonate. The residue in the Buchner funnel was washed with 500 ml of hot dimethyl formamide. The combined filrate was divided in 3 equal portions and each portion poured into a stirred 5-gallon plastic pail containing 3 gallons of demineralized $H_2O$ and 175 ml of concentrated hydrochloric acid. After adjusting the pH to 6, the contents of the pail were cooled. Water from the pail was decanted. The crude product, a viscous material thus obtained, was washed two times with water—1 gallon each time. The powdery material thus obtained was filtered and washed free of acid with demineralized water. The crude product was dried under vacuum at 90° C. overnight—(m.p. 125°–130° C.).

The crude product obtained from the reaction (larger scale, 3 mole basis) contained bis(4-hydroxyphenyl thio)benzene and 4'-bromo-4-hydroxy diphenylsulfide in the ratio of 55/45 (weight %).

To remove 4'-bromo-4-hydroxydiphenyl sulfide, the crude reaction product was slurried with hot cyclohexane for 2 hours, and the resultant mixture was filtered. It required 3 similar extractions to separate 4'-bromo-4-hydroxydiphenyl sulfide from the bis(4-hydroxyphenyl thio)benzene. 4'-bromo-4-hydroxydiphenyl sulfide in white flakes (390 g)—(m.p. 78°–79° C.)—was obtained after removal of cyclohexane from the extract. The insoluble portion of 398 g was found to be 99% bis(4-hydroxyphenyl thio)benzene—(m.p. 158°–160° C.). The infrared (IR) and nuclear magnetic resonance (NMR) spectra of the bis(4-hydroxyphenyl thio)benzene and 4'-bromo-4-hydroxydiphenyl sulfide were consistent with the assigned structures. Elemental analysis given below is also consistent for the two products.

Bis(4-Hydroxyphenyl Thio)Benzene: Molecular formula: $C_{18}H_{14}S_2O_2$ (molecular weight 326.292); Theory: % C: 66.26; % H: 4.32; % S: 19.6; Found: % C: 64.32; % H: 3.98; % S: 18.84.

4'-Bromo-4-Hydroxydiphenyl Sulfide: Molecular formula: $C_{12}H_9BrSO$ (Molecular weight 281.192); Theory: % C: 51.25; % H: 3.23; % S: 11.38; % Br: 28.45; Found: % C: 51.36; % H: 3.22; % S: 11.32; % Br: 28.43.

EXAMPLE 2

Preparation of a Copolycarbonate Produced from Bisphenol A and Bis(4-Hydroxyphenyl Thio)Benzene A copolycarbonate resin was prepared by reacting a mixture of the disodium salts of 2,2-bis(4-hydroxyphenyl)propane (bisphenol A) and bis(4-hydroxyphenyl thio)benzene with phosgene in accordance with the interfacial polycondensation synthesis. 5 weight % of bis(4-hydroxyphenyl thio)benzene and 95 weight % of bisphenol A, based on the weight of the diphenols, were used. The properties measured for this copolycarbonate are reported in Table 1.

TABLE 1

|  | UNITS | | VALUE | |
|---|---|---|---|---|
|  | SI | US Conv | SI | US Conv |
| Izod Impact Strength[1] | J/M | ft lb/in |  |  |
| ⅛" thickness |  |  | 817 | 15.30 |
| ¼" thickness |  |  | 145 | 2.71 |
| Critical Thickness | mm | mil | 4.95 | 195 |
| Melt Index[2] | g/10 min |  | 6.70 |  |
| Heat Deflection Temp[3] |  |  |  |  |
| Under Load °C. | 3 |  |  |  |
| (264 psi) 1.82 MPa | °C. | °F. | 120.8 | 250 |
| Tensile Properties[4] |  |  |  |  |
| Tensile strength at yield | MPa | psi | 61 | 8800 |
| Tensile strength, ultimate | MPa | psi | 61 | 8800 |
| Tensile strength, failure | MPa | psi | 49 | 7100 |
| Elongation, yield % |  |  | 8 |  |
| Elongation, fail % |  |  | 103 |  |
| Flexural Properties[5] |  |  |  |  |
| Strength | MPa | psi | 86 | 12422 |
| Ultimate | MPa | psi | 86 | 12422 |
| Modulus | GPa | psi | 2.3 | 334000 |
| Flammability Properties |  |  |  |  |
| UL-94[6] 3.2 mm (⅛" thickness) |  |  | 94V-2 |  |
| Oxygen Index[7] | % |  | 23.9 |  |
| Optical Properties[8] |  |  |  |  |
| % Brightness |  |  | 83.26 |  |
| % Yellowness Index at 550° F. molding |  |  | 11.8 |  |
| % Haze at 550° F. molding |  |  | 2.2 |  |
| % Yellowness at 650° F. molding |  |  | 17.4 |  |
| % Brightness at 650° F. molding |  |  | 80.5 |  |
| Melt Viscosity, 300° C. | Pa's | Poise |  |  |
| 7.2 $S^{-1}$ |  |  | 620 | 6200 |
| 14.4 |  |  | 600 | 6000 |
| 36.0 |  |  | 540 | 5400 |
| 72.00 |  |  | 510 | 5100 |
| 144 |  |  | 510 | 5100 |
| 360 |  |  | 440 | 4400 |
| 720 |  |  | 360 | 3600 |
| 1440 |  |  | 290 | 2900 |
| Melt Stability, 300° C. | Pa's | Poise |  |  |
| 5 min |  |  | 510 | 5100 |
| 35 min |  |  | 370 | 3700 |
| 65 min |  |  | 350 | 3500 |
| (5–65) |  |  | 160 | 1600 |
| Initial RV |  |  | 1.292 |  |

TABLE 1-continued

| | UNITS | | VALUE | |
|---|---|---|---|---|
| | SI | US Conv | SI | US Conv |
| After 65' strand RV | | | 1.279 | |

[1]ASTM D-256
[2]ASTM D-2138; at 300° C. and 1200 g load
[3]ASTM D-648/72
[4]ASTM D-638
[5]ASTM D-790
[6]Underwriters Laboratories, Inc. 94: Standard For Tests For Flammability Of Plastic Materials For Parts In Devices And Appliances
[7]ASTM D-2863
[8]ASTM D-1003

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of the monomer of the structural formula

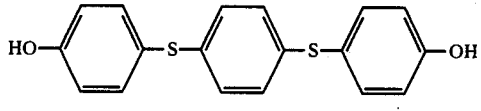

which comprises
(a) reacting 4-mercaptophenol with p-dibromobenzene in the presence of potassium carbonate and dimethyl formamide to form an impure product comprising bis-(4-hydroxyphenyl thio)-benzene and 4'-bromo-4-hydroxydiphenyl sulfide and
(b) removing 4'-bromo-4-hydroxydiphenyl sulfide from said impure product by extraction with cyclohexane and recovering said monomer in purified form.

2. The process of claim 1 wherein said monomer has a purity of about 99% by weight.

* * * * *